(12) United States Patent
Cottingham et al.

(10) Patent No.: US 7,030,289 B2
(45) Date of Patent: Apr. 18, 2006

(54) STABILIZATION OF MILK FROM TRANSGENIC ANIMALS

(75) Inventors: Ian Robert Cottingham, Midlothian (GB); Graham Edward McCreath, Edinburgh (GB)

(73) Assignee: PPL Therapeutics (Scotland) Ltd, Roslin (GB)

( * ) Notice: Subject to any disclaimer, the term of this patent is extended or adjusted under 35 U.S.C. 154(b) by 0 days.

(21) Appl. No.: 09/861,399

(22) Filed: May 18, 2001

(65) Prior Publication Data

US 2003/0088881 A1  May 8, 2003

Related U.S. Application Data

(63) Continuation of application No. PCT/GB99/03868, filed on Nov. 19, 1999.

(60) Provisional application No. 60/128,546, filed on Apr. 9, 1999, now abandoned.

(30) Foreign Application Priority Data

Nov. 19, 1998  (GB)  .................................... 9825374

(51) Int. Cl.
*C12N 5/00* (2006.01)
*C12N 15/00* (2006.01)
*C12P 21/06* (2006.01)

(52) U.S. Cl. ........................... 800/7; 435/69.1; 800/14; 800/15; 800/16; 800/17; 800/18; 800/25

(58) Field of Classification Search ............... 800/4, 800/7, 21, 24, 14, 15, 16, 17, 18, 25; 435/455, 435/463, 320.1, 325, 69.1
See application file for complete search history.

(56) References Cited

FOREIGN PATENT DOCUMENTS

| WO | WO88/00239 | 1/1988 |
|---|---|---|
| WO | WO 92/11358 | 7/1992 |
| WO | WO 94/19935 | 9/1994 |
| WO | WO 95/22249 | 8/1995 |
| WO | WO 96/09377 | 3/1996 |
| WO | WO96/34966 | 11/1996 |
| WO | WO 97/34628 | 9/1997 |

OTHER PUBLICATIONS

Rudolph. Tibtech, 17:367-374 (1999).*
Houdebine. Transgenic Res., 9:305-320 (2000).*
Wright et al. Bio/Tech. 9:830-834 (1991).*
Carver et al. Bio/Tech., 11:1263-70 (1993).*
Djie et al. Jour. Biol. Chem., 272(26):16268-16273 (1997).*
Clark et al., "Pharmaceuticals From Transgenic Livestock", (1987) *Tibtech*, vol. 5, pps 20-24.
Siebenlist, et al.: "Evidence for Intramolecular Cross-Linked Aα•γ Chain Heterodimers in Plasma Fibrinogen," *Biochemistry*, vol. 35, pp. 5817-5821, (1996).
Prunkard, et al.: "High-level Expression if Recombinant Human Fibrinogen in the Milk of Transgenic Mice," *Nature Biotechnology*, vol. 14, pp. 867-871, Jul. 1996.
Wilkins, et al.: "Isolation of Recombinant Proteins from Milk," *Journal of Cellular Biochemistry*, vol. 49, pp. 333-338 (1992).
Butler, et al.: "Current Progress in the Production of Recombinant Human Fibrinogen in the Milk of Transgenic Animals," *Thrombosis and Haemostatis*, vol. 78 (1), pp. 537-542, (1997).
David H. Sierra: "Fibrin Sealant Adhesive Systems: A Review of Their Chemistry, Material Properties and Clinical Applications," *Journal of Biomaterials Applications*, vol. 7, pp. 309-352, Apr. 1993.

* cited by examiner

*Primary Examiner*—Anne-Marie Falk
*Assistant Examiner*—Thaian N. Ton
(74) *Attorney, Agent, or Firm*—Drinker Biddle & Reath LLP; Daniel A. Monaco

(57) ABSTRACT

The present invention relates to the stabilization of milk from transgenic animals. In particular, the invention relates to the protection of proteins (e.g. fibrinogen) expressed in milk from transgenic animals by co-expression of a serine proteinase inhibitor (e.g., $\alpha_1$-antitrypsin) in the milk of the transgenic animals.

2 Claims, 9 Drawing Sheets

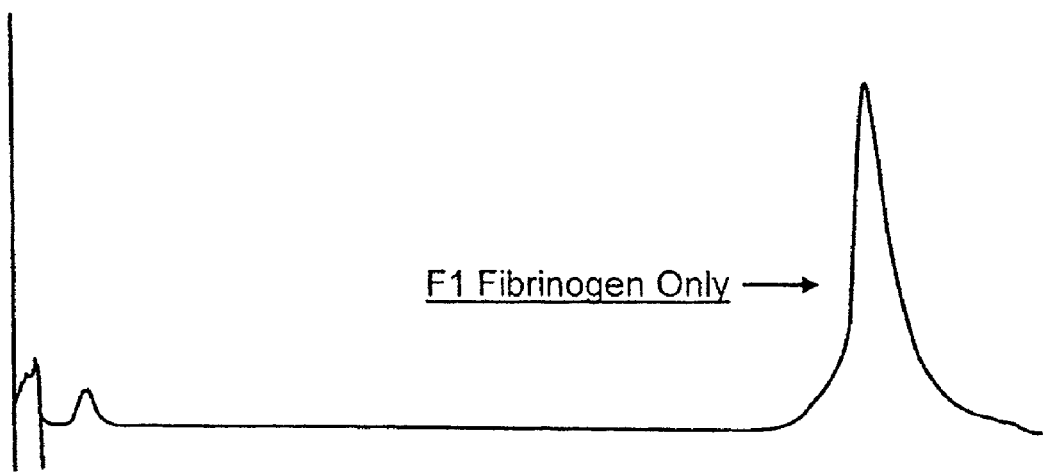
FIG. 14
FIG. 15
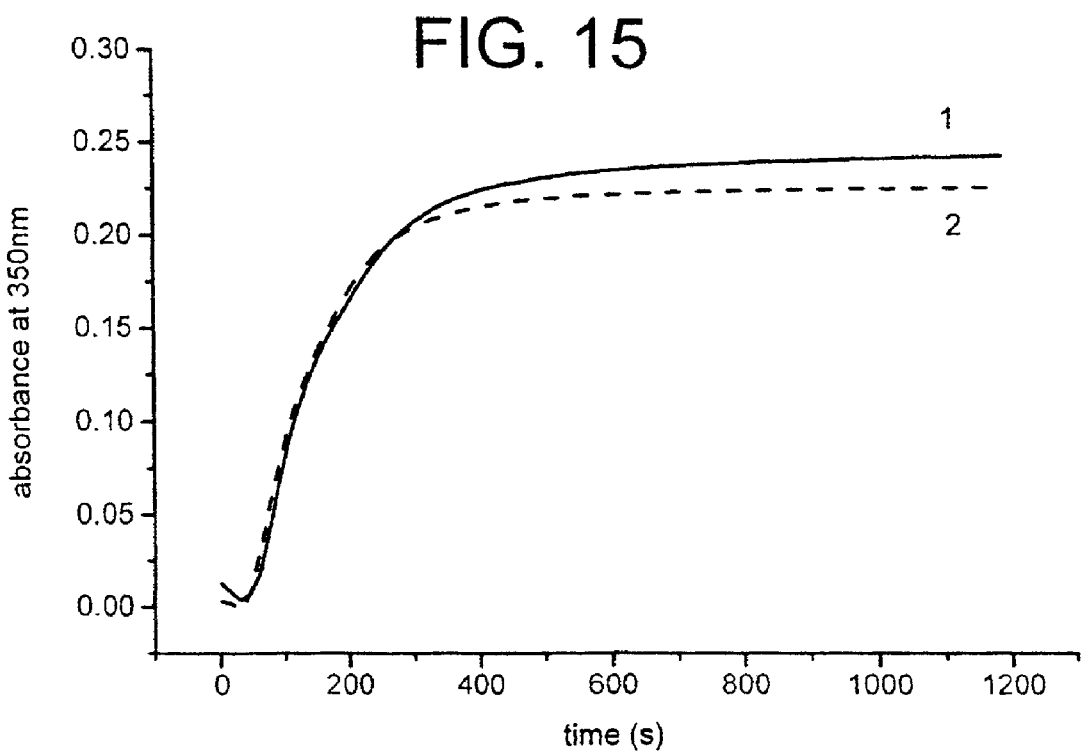

STABILIZATION OF MILK FROM TRANSGENIC ANIMALS

This is a continuation of international application PCT/GB99/03868, published in English, having an international filing date of Nov. 19, 1999, which claims the benefit under U.S.C. 119(e) of the filing date of U.S. provisional application Ser. No.60,128,546, filed Apr. 9, 1999, abandoned.

This invention relates to the stabilization of milk from transgenic animals. In particular, this invention relates to the protection of fibrinogen expressed in the milk of transgenic animals together with the expression of a serine proteinase inhibitor.

Recombinant DNA technology has been used increasingly over the past decade for the production of commercially important biological materials. To this end, the DNA sequences encoding a variety of medically important human proteins have been cloned.

Although the expression of DNA sequences in bacteria to produce the desired medically important protein looks an attractive proposition, in practice the bacteria often prove unsatisfactory as hosts because in the bacterial cell foreign proteins are unstable and are not processed correctly.

Recognising this problem, the expression of cloned genes in mammalian tissue culture has been attempted and has in some instances proved a viable strategy. However batch fermentation of animal cells is an expensive and technically demanding process.

The use of transgenic animals as hosts has been identified as a potential solution to the above problem. WO-A-8800239 discloses transgenic animals which secrete a valuable pharmaceutical protein into their milk. To date, the production of transgenic proteins in the milk of transgenic animals has been successful, with little association of proteolytic damage to the protein by other components of the milk. Practical precautions applied to date against degradation of foreign proteins in milk have been rapid processing of the milk after collection or addition of well-known chemical inhibitors to the milk after collection.

Milk is a complex mixture of proteins, lipids and carbohydrates. The protein component contains essentially three classes of proteins, the caseins, serum proteins and acidic whey proteins. The caseins are assembled into large molecular mass complexes called micelles which can be precipitated by low speed centrifugation or under mild acid conditions. The serum proteins consist primarily of albumin and immunoglobulins although there are small quantities of other proteins including probably the protease precursors plasminogen and prothrombin. The whey proteins tend to be small and acid stable and do not precipitate under acid conditions.

Proteolytic activity can be detected in milk under certain circumstances especially when the natural composition is altered or after extremes of environmental conditions such as heat treatment or prolonged storage. The most significant of these is plasmin which is a protease active under alkaline conditions which cuts proteins after the basic amino acids lysine and arginine. Another protease in milk has thrombin-like activity and is more active under acidic conditions.

The plasmin in milk is in two forms, predominantly the inactive precursor plasminogen and to a lesser degree the active from. The source of this protease is not clear although some of it certainly leaks in to the lumen of the gland from the plasma. Leakage from the plasma is supported by the observation that the levels of plasmin/plasminogen are high in colostrum when it is possible that the barrier between the blood and milk is more leaky and there is a high degree of protein transport into the milk. However, it has also been observed that the level of plasmin/plasminogen also increases during the course of lactation, at least in cows which have been most studied, with a steep rise towards the very end. The final rise in activity has been associated with the proteolytic processes involved in involution of the mammary gland as the tissue begins to undergo the process of shutting down milk production. This is a reasonable assumption since plasmin activity is associated with remodelling processes. In addition to existing in two forms in milk, plasminogen is also predominantly associated with the casein micelles which may form part of a natural mechanism for preventing activation.

Although it has always been a theoretical possibility that the proteases known to be present in milk could act to damage Heterologous proteins expressed to provide a source of therapeutic products, a significant degree of damage—such as would prevent economic production of the target protein—has not been widely evident. Although many proteins have been expressed in mouse milk, as a test system to evaluate expression levels, and mouse milk often contains blood because of the trauma induced during the mechanical process of collecting milk, there have been very few reports of extensive proteolytic damage of the target protein. For instance, a modified tissue plasminogen activator, a protein designed to be proteolytically activated and also a powerful activator of plasminogen, has been successfully expressed in the milk of both mice and goats. This is an especially good demonstration of the general stability of milk since the presence of active plasminogen activator would be expected to activate all of the plasmin activity in milk and possibly cause breakdown of the milk itself. This was not observed in the test systems described.

However, it has now been identified that when human fibrinogen is expressed in the milk of transgenic farm animals there is a surprising degree of proteolytic damage. This is despite the general observations that sheep milk is not high in protease activities, as reported as long ago as 1989 when human plasma factor IX spiked into sheep milk was not found to be degraded (Clark et al, 1989), and despite the successful expression of a number of heterologous proteins—including AAT (alpha-1-antitrypsin), factor IX, factor VII, and bile salt stimulated lipase—without the identification of excessive proteolytic degradation. This experience with sheep milk is repeated with proteins expressed in the milk of other ruminants. In goats for instance, both AAT and anti-thrombin III, a variant tissue plasminogen activator and at least two monoclonal antibodies have been expressed with no reports of proteolytic damage causing problems with the economic recovery of product.

Proteolysis of fibrinogen takes a number of forms and occurs to varying degrees. The alpha chain has a relatively long carboxy terminal region which in its intact form is probably somewhat protected from proteolysis by association with the fibrinogen molecule as a whole. Clipping of the alpha chain, once it occurs, tends to be progressive presumably because the carboxy region becomes more exposed in the solution phase and more accessible to proteases. Indeed, fibrinogen isolated from human plasma already has some proteolysis of the alpha chain, at least one of the two subunits present, and the entire fibrinogen molecule runs as a doublet, known as F1, the parent molecule, and F2, with partial alpha chain degradation. Further proteolysis leads to clipping of the two alpha chains per molecule but there is also a progressive clipping back of the alpha chains leading to the appearance of 'Fragment X' which has relatively extensive damage of both chains. Yet more proteolysis now occurs on the damaged molecule leading to a molecular mass 'ladder' of smaller species; Fragments Y, D etc. Functionality of the clotting ability begins to be substantially reduced at the stage of Fragment X and beyond. The presence of this fragment is therefore a useful measure of the proportion of functional fibrinogen present in a mixture and it is desirable—with regard to recovering a useful product—to keep the Fragment X content to a minimum.

The site of damage to the alpha chain seen in the F2 component of human plasma is not consistent with the known specificity of plasmin and does not occur at a single position. Despite this, one of the biological functions of plasmin is to degrade the fibrin component of blood clots and it is known that fibrinogen, before activation by thrombin and incorporation into a blood clot, can be damaged in the alpha chain by plasmin. It is therefore possible that plasmin in milk could produce partial degradation of fibrinogen to produce F2 and subsequent degradation to X.

It is generally expected that the higher the level of expression of a heterologous protein in milk, the lower the degree of proteolytic damage of that protein. However, even at a total expression level of about 5 grams per litre in sheep milk, there is an obvious and substantial proportion of Fragment X observable by gel analysis. This has the effect of reducing the level of recoverable fibrinogen and necessitating the removal of fragments below F2 by any process designed to recover functional product. The degree of fibrinogen damage in milk is much higher than expected based on the experience with other proteins. Thus, fragment X has been observed at all stages of lactation, beginning at a high level in colostrum, decreasing during the first thirty days of lactation and then steadily increasing during the next thirty days. A further complexity with fibrinogen is the effect of a second protease activity in milk which has a thrombin-like effect, in removing the fibrinopeptides A and B, and increasing the tendency of fibrinogen to self-aggregate and become insoluble, at least under non-denaturing conditions—such as would be used in a process designed to produce a biologically active material.

Both the plasmin and thrombin activities in milk, which have never before appeared to hamper the recovery of heterologous proteins expressed in ruminant milk, have a substantial impact on reducing process yields of fibrinogen, necessitating a more complex—and therefore more expensive—recovery process and shortening the useful storage life of milk. This is a combination of irretrievable material lost by precipitation and degraded material which must be removed to yield functional fibrinogen. The overall effect is that purification yields are low during the first fifteen days of lactation, increase and stay high for the next thirty to forty days and then drop rapidly as the lactation proceeds. This cuts down the normal useful supply of milk from a lactation from perhaps more than four months by nearly a third and thus increases the cost of providing milk by a factor of at least three. Furthermore, the present of a substantial proportion of Fragment X necessitates larger column matrix volumes and a fundamentally more complex process. It is of obvious benefit, in terms of the economic recovery of recombinant fibrinogen from the milk of transgenic sheep, or other mammals, if a method can be found to substantially decrease the proteolytic damage to the molecule both during expression in the milk, during storage of the milk and during subsequent processing.

Controlling proteolysis in stored milk and during processing can theoretically be addressed by the addition of protease inhibitors immediately after milk collection. However, it must be borne in mind that the product is intended for therapeutic use in humans and therefore, the risks of adding protease inhibitors—which are often by nature toxic as an intrinsic property of being inhibitors—and the costs of monitoring and removal must be considered realistically. A further complication with respect to fibrinogen is that there appear to be two different proteases which are responsible, in combination, for the loss of yield. Most of the inhibitors which are acceptable from a therapeutic processing viewpoint—which excludes the active-site serine alkylating agents such as diisoproplyfluorophosphate—are unlikely to work effectively against both activities further complicating the process and safety issues.

One inhibitor tested from a range of possible candidates, which is effective against plasmin, namely tranexamic acid, has been found to be effective in stabilising milk during storage but this does not affect this initial level of Fragment X or prevent thrombin damage. In a similar experiment, which looked at the level of Fragment X generated on incubation of transgenic milk at elevated temperature, AAT at 1 gram per litre was itself found to be ineffective.

A second and hitherto unexplored approach to reducing or curtailing further loss of useful product due to proteolysis is to co-express a protease inhibitor with the product in the milk of the producer species. To date there has been no motivation to do this because the problem of proteolytic damage of heterologous expressed proteins in the milk of transgenic animals, to the level which required prevention over and above those means already identified in the art, had not been recognised. However, there are problems in the choice of inhibitor in the absence of scientific certainty as to the exact identity of the proteases causing the damage and their relative contribution to that damage. For instance, it is possible to select an inhibitor of plasmin, for instance the serpin alpha-2 antiplasmin, which is highly active against plasmin, but has little effect on thrombin. This could be co-expressed with fibrinogen but may not protect against thrombin which could still cause extensive precipitation-related losses or damage the final product and adversely affect its stability. Expression of a potent plasmin inhibitor in the mammary gland may also have unpredictable effects on morphological development or milk production since there is a possible role of plasmin in gland biology.

Conversely, it would be possible to express antithrombin III and inhibit thrombin damage to fibrinogen but this would be ineffective against plasmin and possibly other proteases contributing to the overall damage of the target molecule. None of the above protease inhibitors would thus be recognised as suitable "protective proteins" in the production of therapeutically useful proteins in the milk of transgenic animals.

The protease inhibitor AAT is hardly effective as an inhibitor against either plasmin or thrombin because of its narrow protease specificity (see Example 1 and FIG. 1). The natural target protease for AAT acting as an inhibitor is elastase. It is not reported that the protease elastase occurs in milk except during infection when neutrophils, which can release large quantities of elastase, are present. It is unlikely that this protease is the cause of proteolytic damage to fibrinogen made in sheep milk because any animal which suffers mastitis, or other mammary infection, is withdrawn from the milking flock. Furthermore, AAT has previously been shown by the present inventors not to affect the stability of transgenic fibrinogen when added to the transgenic milk after collection. This is in contrast to the stabilising effect of the plasmin inhibitor tranexamic acid when added to the transgenic milk after collection. Accordingly, AAT, along with the other protease inhibitors described above would not be expected to provide any protective effect when produced in the milk of transgenic animals.

Having established the case that the above serine protease inhibitors are unlikely candidates to be effective in preventing the proteolysis of fibrinogen if co-expressed in the mammary gland of a transgenic animal, the dramatic and therefore surprising protective effect of such co-expression is the basis of this invention. In the example given, AAT and fibrinogen co-expression was promoted by cross-breeding two separate lines. The resulting fibrinogen, as analysed from induced lactations, was remarkably different from fibrinogen expressed in the absence of AAT. The main difference was that the alpha chain of fibrinogen co-expressed with AAT had undergone none or very little detectable proteolytic processing. This was shown by the presence of predominantly the F1 species on a non-reducing gel, an observation which was confirmed after partial purification by precipitation followed by hydrophobic interaction chromatography—which can separate F1 and F2 into distinct components—and by the presence of predominantly a single alpha chain species in place of the normal doublet on reducing gel analysis (see Example 4c and FIG. 10). A second demonstration of the apparent reduction of proteolysis was the absence of Fragment X on non-reducing gel analysis which is normally seen in induced milk, and natural milk, of fibrinogen-only lines.

According to a first aspect of the present invention, there is provided the use of a serine proteinase inhibitor which is expressed in the milk of a transgenic non-human animal to stabilise the milk. The present invention provides, by such use, prolonging the storage of milk which is particularly useful where the milk contains a therapeutically valuable protein. The stabilisation of the milk in particular relates to the reduced proteolytic damage of proteins in the milk.

As used herein, "milk" is understood to be the fluid secreted from the mammary glands in animals. The stabilisation of the milk is predominantly in respect of reduced proteolytic damage. The levels of the serine proteinase inhibitor required to achieve the stabilising effect will vary somewhat, but can be easily determined by the skilled person by standard procedures and without undue burden. Factors to take into consideration include, the type of serine proteinase inhibitor and the animal in which the serine proteinase is being expressed. The levels of the serine proteinase inhibitor in the milk include those levels which are elevated above any background or endogenous level, for example an increased level of expression from an introduced transgene or from an endogenous gene which has been modified to raise levels The serine protease inhibitor are preferably those of the serpin or kunitz families, in particular antithrombin III, heparin cofactor II, alpha-2-antiplasmin, protease nexin-I, preferably alpha-1-antichymotrypsin, most preferably alpha-1-antitrypsin.

The serine protease inhibitors of the present invention include a number which are well known in the art and many of which have already been cloned and expressed transgenically. Their use in the present invention is particular in that their expression is not predominantly for isolation as useful proteins in themselves but as protective proteins in the stabilisation of milk, in particular milk which contains a heterologous protein, the purpose of which is for isolation as a therapeutically useful ingredient. Accordingly, the serine protease which is expressed can be in any form which provides a protective capability. The serine proteinase according to the first aspect of the invention includes all naturally occurring forms of the proteins as well as other related species, including truncated proteins, amino acid sequence variants (muteins or polymorphic variants) and species which comprise additional residues and any naturally occurring variants thereof.

The serine proteinase inhibitor may be endogenous or exogenous to the animal. If it is endogenous, there will have been some modification to the animal to "switch on" its expression which includes expression in the animal's milk. If the serine proteinase is exogenous to the animal (i.e. a transgene) then it may be from any source. Preferably the serine proteinase inhibitor is bovine, ovine or human derived.

Of particular interest in the present invention is the proteinase inhibitor alpha-1-antitrypsin. Alpha-1-antitrypsin (AAT) comprises 394 amino acids as a mature peptide. It is initially expressed as a 418 amino acid pre-protein. The mRNA coding for the pre-protein is 1.4 kb long, and this corresponds approximately to the length of the cDNA coding for AAT used in the present application (approximately 1.3 kb). The structural gene (liver version, Perlino et al, The EMBO Journal Volume 6 p.2767–2771 (1987)) coding for AAT contains 4 introns and is 10.2 kb long. As described above, the AAT according to the invention need not be in its naturally occurring form. Examples include oxidation-resistant mutants and other analogues of serine protease inhibitors such as AAT. These analogues include novel protease inhibitors produced by modification of the active site of alpha-1-antitrypsin. For example, if the Met-358 of AAT is modified to Val, this replacement of an oxidation-sensitive residue at the active centre with an inert valine renders the molecule resistant to oxidative inactivation.

The animal according to the first aspect of the invention may be a sheep, cow, goat, rabbit, mouse, camel, water-buffalo, pig or horse.

The stabilisation according to the first aspect of the invention can be extended to the stabilisation of a heterologous protein also expressed in the milk of the non-human animal.

In order to obtain the desired expression in the milk of a transgenic animal it will be necessary to change the genomic configuration of the animal. It may be necessary to introduce the serine proteinase inhibitor (and any other heterologous protein also for expression in the milk) under the control of a milk protein gene promoter. The milk protein gene promoter may be any, including those known in the art, such as the long or short whey acid protein promoter, the alpha-lactalbumin promoter, the short or long $\alpha$, $\beta$ or kappa casein promoter, but the beta-lactoglobulin gene promoter is particularly preferred. The promoters are selected on the basis of a number of factors, such as the composition of various milks of different animals. For example, the sheep BLG promoter is particularly useful in expressing proteins in the sheep mammary gland. Details of the genes and their promoters have been published such as Clark et al, TIBTECH 5:20 (1987) and Henninghausen, Protein Expression and Purification 41:3 (1990).

The 5' flanking sequence (as part of the milk gene promoter) will generally include the mink protein, e.g. beta-lactoglobulin (BLG) transcription start site. For BLG it is preferred that about 800 base pairs (for example 799 base pairs) upstream of the BLG transcription start site be included. In particularly preferred embodiments, at least 4.2 kilobase pairs upstream are included.

Suitable 3'-sequences may be present. It may not be essential for such sequences to be present, however, particularly if the protein-coding DNA comprises its own polyadenylation signal sequence. However, it may be necessary or convenient in some embodiments of the invention to provide 3'-sequences. The 3' untranslated region apparently stabilizes the RNA transcript of the expression system and thus increases the yield of the desired protein. Such sequences may be derived from the casein 3' untranslated region, the SV40 small and antigen, the 3' untranslated region of other milk protein genes, in particular the BLG gene 3' untranslated region.

Appropriate signal and/or secretory sequence(s) may be present if necessary or desirable. In this regard both homologous and heterologous regulatory sequences are useful in the present invention. Among the useful sequences that regulate transcription, in addition to the promoters discussed above, are enhancers, splice signals, transcription termination signals and polyadenylation sites, many of which are known in the art.

The species of animals selected for expression is not particularly critical, and will be selected by those skilled in the art to be suitable for their needs. Mammals are preferred and may be essential. Suitable laboratory mammals for experimental ease of manipulation include mice and rats. Larger yields may be had from domestic farm animals such as cattle, pigs, water buffalo, camels, goats and sheep. Intermediate between laboratory animals and farm animals are such animals as rabbits are also suitable.

Throughout the whole of this document, we use the term "transgenic" in a broader sense to include animals which carry any type of genetic modification (e.g. gene deletion, mutation, substitution) effected, at some stage, by genetic manipulation in vitro, The genetic manipulation may have been carried out on the animal itself during some stage, or may have been carried out on an animal which was involved in the production of the animal (e.g. a parent animal). Accordingly, not only are the first generation of animals protected by the present invention, so also are progeny thereof which also carry the required genetic modification as described above. The term "transgenic" also includes animals which have been manipulated such that an endogenous or an exogenous gene which is either "switched on" or its levels of expression is "switched up", usually by introduction or rearrangement of a promoter sequence in the genome of the animal.

According to a second aspect of the invention, there is provided the use of a non-human transgenic animal which is capable of expressing a serine proteinase inhibitor in its mammary gland in the production of stabilised milk.

According to a third aspect of the invention there is provided the use of a non-human transgenic animal, which has stably integrated into its genome an exogenous DNA sequence encoding a serine proteinase inhibitor in the production of stabilised milk.

In the second and third aspects of the invention, the non-human transgenic animal preferably lactates and produces milk. All preferred features of the first aspect of the invention apply to the second and third.

In accordance with all aspects of the invention a transgenic animal is preferably capable of transmitting the construct to its progeny.

According to a fourth aspect of the invention, there is provided a non-human transgenic animal which is capable of expressing a serine proteinase inhibitor and fibrinogen in its milk.

According to a fifth aspect of the invention there is provided a non-human transgenic animal having stably introduced into its genome, an exogenous DNA sequence encoding a serine proteinase inhibitor and an exogenous DNA sequence encoding fibrinogen.

Preferably, according to the fourth and fifth aspects of the invention, the non-human transgenic animal is capable of co-expressing the serine proteinase inhibitor and the fibrinogen in its milk. As an alternative, the serine proteinase inhibitor may be expressed earlier than the fibrinogen, but should also be expressed simultaneously as the fibrinogen is expressed. In order that the serine proteinase inhibitor and the fibrinogen are expressed in the mammary gland of the animal, the coding sequences are preferably under the control of one or more milk gene promoter.

Fibrinogen has been identified as a suitable protein according to the present invention as it has now been identified as being proteolytically vulnerable when expressed as a transgenic protein in the milk of a transgenic animal.

Fibrinogen, the main structural protein in the blood responsible for the formation of clots exists as a dimer of three polypeptide chains; the A$\alpha$ (66.5 kD), B$\beta$ (52 kD) and $\gamma$ (46.5 kD) are linked through 29 disulphide bonds. The addition of asparagine-linked carbohydrates to the B$\beta$ and $\gamma$ chains results in a molecule with a molecular weight of 340 kD. Fibrinogen has a trinodal structure. A central nodule, termed the E domain, contains the amino-termini of all 6 chains including the fibrinopeptides (Fp) while the two distal nodules termed D domains contain the carboxy-termini of the A$\alpha$, B$\beta$ and $\gamma$ chains. Fibrinogen is proteolytically cleaved at the amino terminus of the A$\alpha$ and B$\beta$ chains releasing fibrinopeptides A and B (FpA & FpB) and converted to fibrin monomer by thrombin, a serine protease that is converted from its inactive form by Factor Xa. The resultant fibrin monomers non-covalently assemble into protofibrils by DE contacts on neighbouring fibrin molecules. This imposes a half staggered overlap mode of building the fibrin polymer chain. Contacts are also established lengthwise between adjacent D domains (DD contacts) leading to lateral aggregation. Another serine protease, Factor XIII is proteolytically cleaved by thrombin in the presence of $Ca^{2+}$ into an activated form. This activated Factor XIII (Factor XIIIa) catalyses crosslinking of the polymerised fibrin by creating isopeptide bonds between lysine and glutamine side chains. The first glutamyl-lysyl bonds to form are on the C-terminal of the $\gamma$ chains producing D—D crosslinks. Subsequently, multiple crosslinks form between adjacent A$\alpha$ chains, the process of crosslinking imparts on the clot both biological stability (resistance to fibrinolysis) and mechanical stability [Sienbenlist and Mosesson, Progressive Cross-Linking of Fibrin $\gamma$ chains Increases Resistance to Fibrinolysis, Journal of Biological Chemistry, 269: 28414–28419, 1994].

The coagulation process can readily be engineered into a self sustained adhesive system in vitro by having the fibrinogen and Factor XIII as one component and thrombin and $Ca^{2+}$ as the second component which catalysis the polymerisation process. These adhesion systems, known in the art as "Fibrin Sealents" or "Fibrin Tissue Adhesives" have found numerous application in surgical procedures and as delivery devices for a range of pharmaceutically active compounds [Sierra, Fibrin Sealant Adhesive Systems: A Review of Their Chemistry, material Properties and Clinical Applications, Journal of Biomaterials Applications, 7:309–352, 1993].

It has been estimated that the annual US clinical need for fibrin sealents is greatly in excess of the 300 Kg/year that can be harvested using the current cryoprecipitation methods used by plasma fractionaters. Alternative sources of fibrinogen, by far the major component in fibrin sealent, have therefore been explored with recombinant sources being favored [Butler et al., Current Progress in the Production of Recombinant Human Fibrinogen in the Milk of Transgenic animals, Thrombosis and Haemostasis, 78: 537–542, 1997]. It has been shown that mammals are capable of producing transgenic human fibrinogen at levels of up to 5.0 g/L in their milk making this a commercially viable method for the production of human fibrinogen [Prunkard et al., High-level expression of recombinant human fibrinogen in the milk of transgenic mice, Nature Biotechnology, 14:867–871, 1996; Cottingham et al., Human fibrinogen from the milk of transgenic sheep. In: Tissue Sealents: Current Practice, Future Uses. Cambridge Institute, Newton Upper Falls, Mass., March 30 Apr. 2, 1996 (abstract)].

As used herein, the term "fibrinogen" refers to the main structural protein responsible for the formation of clots and includes the whole glycoprotein form of fibrinogen as well as other related fibrinogen species, including truncated fibrinogen, amino acid sequence variants (muteins or polymorphic variants) of fibrinogen, fibrinogen species which comprises additional residues and any naturally occurring variants thereof. The same variations as described above also apply to other fibrinogen-like proteins which can be isolated from milk according to the present invention. The present invention is useful for the production and isolation of individual proteins per se, or proteins which have been altered in some way to facilitate transgenic expression, such as by fusion to other proteins.

The fibrinogen may be from any source, but is preferably bovine or human derived.

As used herein, the term "fibrin adhesive" or "fibrin sealent" describes a substance containing fibrinogen which is capable of forming a biodegradable adhesive or seal by the formation of polymerised fibrin. Such adhesive/sealent systems are alternatively called "fibrin tissue adhesives" or "fibrin tissue glues". The adhesive or seal may act as, inter alia a hemostatic agent, a barrier to fluid, a space-filling matrix or a drug-delivery agent. Particular use may be found in neurosurgery, opthalmic, orthopaedic or cardiothoracic surgery, skin grafting and various other types of surgery.

Other than fibrinogen, the fibrin adhesive or sealent may contain substances which encourage the formation of the fibrin adhesive/seal, such as thrombin, $Ca^{++}$ and Factor XIII (which in this text also includes reference to Factor XIIIa). While it is recognised that thrombin would be the preferred enzyme with which to incorporate into any system whereby the formation of a fibrin clot is desired, it is appreciated that there are other enzymes capable of proteolytically cleaving fibrinogen resulting in the formation of a fibrin clot. An example of this would be the snake venom enzyme Batroxobin [Weisel and Cederholm-Williams, Fibrinogen and Fibrin: Characterization, Processing and Applications, *Handbook of Biodegradable Polymers* (Series: Drug targeting and Delivery) 7:347–365, 1997]. Other components such as alburnin, fibronectin, solubilisers, bulking agents and/or suitable carriers or diluents may also be included if desired.

One advantage of fibrin sealent as a biodegradable polymer is that there are natural mechanisms in the body for the efficient removal of clots and thus the fibrin sealent may be a temporary plug for hemostasis or wound healing. Various proteolytic enzymes and cells can dissolve fibrin depending on the circumstances, but the most specific mechanism involves the fibrinolytic system. The dissolution of fibrin clots under physiological conditions involves the binding of circulating plasminogen to fibrin, and the activation of plasminogen to the active protease, plasmin, by plasminogen activators which may also be, also bound to fibrin. Plasmin then cleaves fibrin at specific sites.

Depending on the situation, it may be advantageous to let the natural process of fibrin breakdown take place after applying a fibrin adhesive or sealent to a site. Indeed, this breakdown may be encouraged, for example, by the inclusion of plasminogen. Alternatively, in some situations it may be advantageous to delay the process by including antifibrinolytic compounds which can, for example, block the conversion of plasminogen to plasmin or directly bind to the active site of plasmin to inhibit fibrinolysis. Such antifibrinolytics include $\alpha_2$-macroglobulin, which is a primary physiological inhibitor of plasmin; aprotinin; $\alpha_2$-antiplasmin; and δ-aminocaproic acid.

The fibrin/sealent may comprise two components, one component containing fibrinogen and Factor XIII (and/or Factor XIIIa) and the other component containing thrombin and $Ca^{++}$. Other substances as described above may be included in one or both of the components if desired.

While the main use of fibrinogen is thought to be for the preparation of adhesive or sealing agents as hereinbefore described, fibrinogen has other applications in the field of medicine, for example as a coating for polymeric articles as disclosed in U.S. Pat. No. 5,272,074. A particular use of lyophilised fibrinogen of the present invention is within or part of a gauze or bandage (preferably made from polylactic acid compounds used in surgical stitches). Such a wound dressing can be supplied (also incorporating the other components required for the formation of a clot (described above), optionally in a package or kit form, for application direct to the skin or to an internal organ.

All preferred features of aspects one to three also apply to the fourth and fifth.

According to a sixth aspect of the invention, there is provided the use of a non-human transgenic animal according to the fourth or fifth aspects of the invention in the production of recombinant fibrinogen. All preferred features of aspects one to five, also apply to the sixth.

According to a seventh aspect of the invention there is provided a process for producing a non-human transgenic animal according to the fourth or fifth aspects of the invention, comprising the steps of:

(a) providing a first DNA sequence or family of sequences encoding a serine proteinase inhibitor;

(b) introducing said DNA sequence or sequences into a cell, zygote or an embryo of an animal capable of generating into a transgenic animal with said first DNA sequence stably integrated into its genome;

(c) providing a second DNA sequence or family of sequences encoding fibrinogen;

(d) introducing said second DNA sequence or sequences into a cell, zygote or an embryo of an animal capable of generating into a transgenic animal with said second DNA sequence stably integrated into its genome;

(e) causing the cell, zygote or embryo to develop into an animal.

In this aspect of the invention, the "first" and "second" DNA sequences may not actually be individual and separate sequences. For example, fibrinogen is often introduced in a process as described above on more than one sequence (a family of sequences), in this case on three separate constructs which encode for the three subunit chains of fibrinogen. The same may also apply to the coding sequence for the serine protease inhibitor.

The first and second sequences may be introduced into the cell, zygote or embryo separately, simultaneously or sequentially. The first and/or second DNA sequences may be operably linked to a milk gene promoter.

In the process according to the seventh aspect of the invention, the animal is preferably induced to lactate.

The process for producing the transgenic animals according to the present invention are not limiting. They include: pronuclear microinjection (first described in 1980, Gordon J W et al., Proc. Natl. Acad. Sci. USA 77: 7380–7384) and described in relation to gene transfer in livestock (Ebert K M and Schindler, J E S, Theriogenology 39, 121–135, 1993); in vitro maturation and fertilisation (Krimpenfort, P. et al., Biotechnology 9, 844–847, 1991); retrovirus mediated gene transfer (Weiss R., et al., *RNA tumour viruses*. Cold Spring Harbour Laboratory, New York 1985); Sperm-mediated DNA transfer, (Bachiller D. et al., Mol. Reprod. Dev. 30, 194–200, 1991); Embryonic Stem cell mediated transgenesis; Embryonic germ cells (Stewart L. C., Dev. Bio. 161, 626–628, 1994); and nuclear transfer, such as described in WO97/07669 and WO97/07668. Microinjection and nuclear transfer are the preferred methods for the production of transgenic animals according to the present invention.

Preferred features of aspects one to six, also apply to the seventh.

An eighth aspect of the invention provides a transgenic animal produced by a process according to the seventh aspect of the invention. All preferred features aspects one to seven, also apply to the eighth.

A ninth aspect of the invention provides a process for producing recombinant fibrinogen comprising;
(a) inducing a transgenic animal, according to the fourth, fifth or eighth aspects of the invention to lactate;
(b) milking the animal;
(c) collecting the milk; and
(d) isolating the fibrinogen, optionally including purification steps.

Isolation of the fibrinogen and subsequent purification can be by any process. Preferred features of aspects one to eight also apply to the ninth.

A tenth aspect of the invention provides recombinant fibrinogen produced in the milk of an animal according to any one of aspects four, five, eight or nine. Preferred features of any one of aspects one to nine, also apply to the tenth.

An eleventh aspect of the invention provides fibrin sealant comprising recombinant fibrinogen according to the tenth aspect of the invention. Details in respect of fibrin sealants are described hereinbefore. All preferred features of aspects one to ten, also apply to the eleventh.

In order to co-express fibrinogen and AAT it is preferable to make expression constructs capable of directing expression at sufficient levels in the same tissue, the mammary epithelial cells, at the same time. This can be achieved by a number of methods using constructs which contain a promoter region, a means of directing tissue specific expression, possibly but not necessarily activated by prolactin, a cDNA or genomic DNA encoding the protein of interest and preferably some means of stabilizing the mRNA transcript, possibly a poly adenosine 3' region. This can be achieved by directing the expression of fibrinogen using three separate constructs, one for each of the three subunits, containing gDNA sequences preceded by a truncated version of the beta-lactoglobulin promoter and followed by a 3' poly A terminator region. The detailed construction of these constructs is described in PCT/US95/02648. The skilled person in this field will know of many other promoters which can direct expression to the mammary tissue using natural mammary-directed control regions, such as those for the alpha-lactalbumin promoter, the WAP promoter or a casein promoter, or artificial promoters with appropriate control elements.

The expression construct for AAT used a similar design with the BLG promoter and a modified gDNA for AAT, with two of the exons fused, as described by Clark et al (Clark et al, 1989. Bio/Technology 7: 487–492). It is standard practice in this field to design constructs with other promoters as described above for fibrinogen. It is also possible to envisage altering the genetic composition of an animal such that its endogenous AAT becomes highly expressed in the mammary gland, for example by 'switching on' the normally inactive genes in the mammary cells.

For both fibrinogen and/or AAT according to the present invention, expression can be engineered using homologous recombination of gDNA or even cDNA inserted into suitable active regions of the transgenic animals genome behind existing promoters.

Transgenic animals can be made using a variety of methods including pro-nuclear microinjection, nuclear transfer to oocytes from transformed cell lines, recombination techniques etc. For instance, animals transgenic for both human fibrinogen and human AAT can be made by mixing equimolar proportions of all four BLG constructs (described above)—one for each of the fibrinogen subunits and one for AAT, after excision from *E. coli* vectors and purification, and injecting the mixture thus created into the pronuclei of sufficient fertilised animals, for example, sheep oocytes to generate a suitable number of transgenic offspring to ensure useful expression levels. In this case useful means a sufficient level of fibrinogen for commercial recovery and sufficient AAT to prevent proteolysis.

An alternative method for making animals transgenic for both fibrinogen and AAT is to cross-breed stable and separate lines expressing each protein individually. For instance, G1 females from a line transgenic for fibrinogen are bred with males transgenic for AAT. If heterozygous AAT males are used then approximately one in eight of the offspring are doubly transgenic females. Therefore, a more efficient route is to breed the fibrinogen transgenic females with homozygous AAT males which results in approximately one in four double transgenic females. Alternatively, the AAT transgenic animals can be female heterozygous bred against heterozygous or homozygous fibrinogen males. Again this will result in approximately one in eight or one in four double transgenic females respectively.

There are many process-related advantages of AAT co-expression fibrinogen-containing milk. This first of these is the stability and storage life of the product in milk. It has been demonstrated that the product remains stable in milk exposed to storage at elevated temperatures whereas fibrinogen expressed alone in milk is further damaged by proteolysis. There are advantages in fibrinogen availability since the concentration in AAT co-expression milk is similar to that in fibrinogen-alone milk but this total expression level, rather than just the intact material present, is available for processing. Similarly, because it is no longer necessary to remove fibrinogen fragments, which can be regarded as closely-related contaminants, from the product, the process can be less complex and use smaller chromatography columns giving substantial scope for reducing overall costs.

There are also product-related advantages for co-expressing fibrinogen. The first advantage is that the resulting product, which can contain a high proportion of intact alpha chain, is highly defined and thus can be accurately formulated to give optimum properties for a fibrin sealant or glue preparation (with added thrombin and factor XIII components as necessary). It is known for instance that an increased proportion of Fragment X adversely affects the desirable physical characteristics of such compositions. It is expected that an increasing proportion of F1 will be beneficial in making both stronger and more flexible fibrin sealant compositions and it may also be possible to make sealants with defined and selected properties at lower fibrinogen concentrations so increasing the economy of manufacture.

A further product-related advantage comes from the observation that fibrinogen undergoes a sort of progression in its vulnerability to proteolysis. Thus, F2 is degraded more readily than F1, Fragment X more readily and extensively than F2 and so on down the ladder of fragments. It is therefore expected that predominantly F1 fibrinogen will be more stable against the action of proteases and therefore have a longer shelf life and be better for the formulation of liquid compositions. A second factor which will extend shelf-life is the effectively protease-free origin of the AAT co-expression fibrinogen. The susceptibility of fibrinogen to proteases in general means that the detrimental effects of any low level protease contamination in the final formulations will severely restrict the storage conditions compatible with prolonged storage, especially in a non-frozen state. The presence of AAT in the starting material means that any active proteases present will be complexed and removed by the process and thus not appear in the product.

The mechanism by which the co-expression of AAT has such a dramatic effect on preventing the proteolytic damage of fibrinogen is unclear in view of the predicted lack of efficacy against the most likely proteases present in milk; plasmin and thrombin. It presumably results from a combination of the constant presence of AAT preventing the build up of even low concentrations of proteases and the prevention thereby of even the slightest damage to the fibrinogen which, if it occurred, would be sufficient to elevate its overall susceptibility to proteolysis. Thus, AAT may not be effective when added to milk because there are already higher and unrestrained protease activities present and the fibrinogen present has already been primed for further proteolytic damage. In the present case, the transgenic animal expresses AAT at about 10 grams per litre of the inhibitor. It may be that such a high AAT concentration, in combination with co-expression, is particularly preferred in the stability of the milk and in the co-expression with fibrinogen.

It should be emphasised that although the protective effects of AAT are unexpected, this does not preclude the possible use of other protease inhibitor proteins to protect heterologous proteins provided that sufficiently high expression levels can be obtained, that their specificity is broad enough to inhibit the responsible proteases and there are no detrimental effects on mammary gland biology or indeed host animal physiology. These limitations can easily be determined by the skilled person without undue experimentation or undue burden. This invention therefore covers the co-expression of other protease inhibitors, especially those of the serpin and kunitz families, for the protection of proteolytically vulnerable heterologous proteins expressed in non-human mammalian milk (such as, for example Factor VIII and tissue plasminogen activator). It is also recognised according to the present invention that the expression of a protease inhibitor protein alone in milk will be of benefit with regard to the storage properties of milk for human consumption and as an aid to processing into further products.

The invention will now be illustrated by a number of examples. The examples refer to the accompanying drawings, in which.

Figure 6:
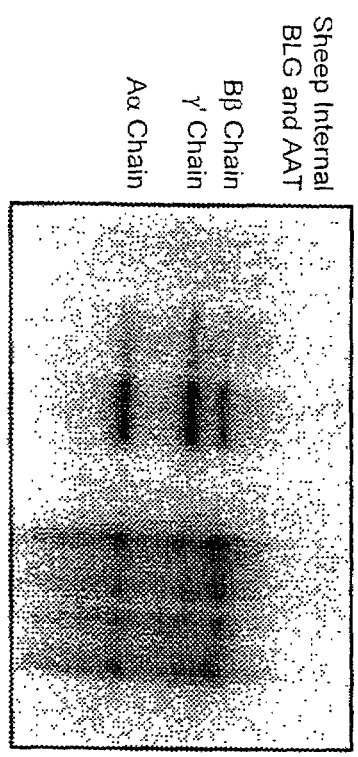

FIG. 6 is a Southern blot, showing the screening of the DNA of sheep a and b, which are transgenic for AAT and fibrinogen. The sheep were screened for fibrinogen. Lane A is a negative control; lane B is a 1 copy control; lane C is a 10 copy control; lane D is sheep a and lane E is sheep b.

Figure 7:
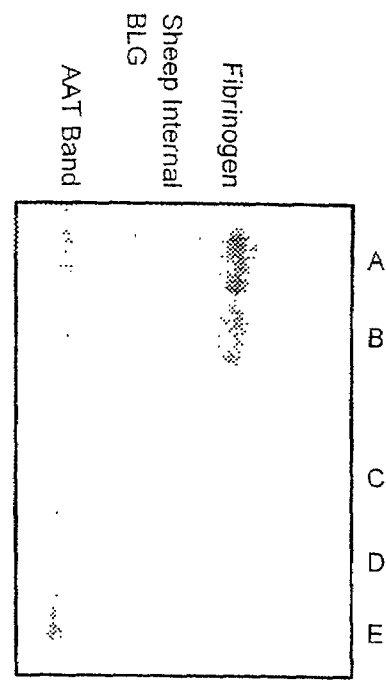

FIG. 7 is a Southern blot, showing the screening of the DNA of sheep a and b, which are transgenic for AAT and fibrinogen. The sheep were screened for AAT. Lane A is sheep 1; lane B is sheep b; lane C is a negative control; lane D is a 10 copy control; lane E is a 20 copy control.

Figure 8:
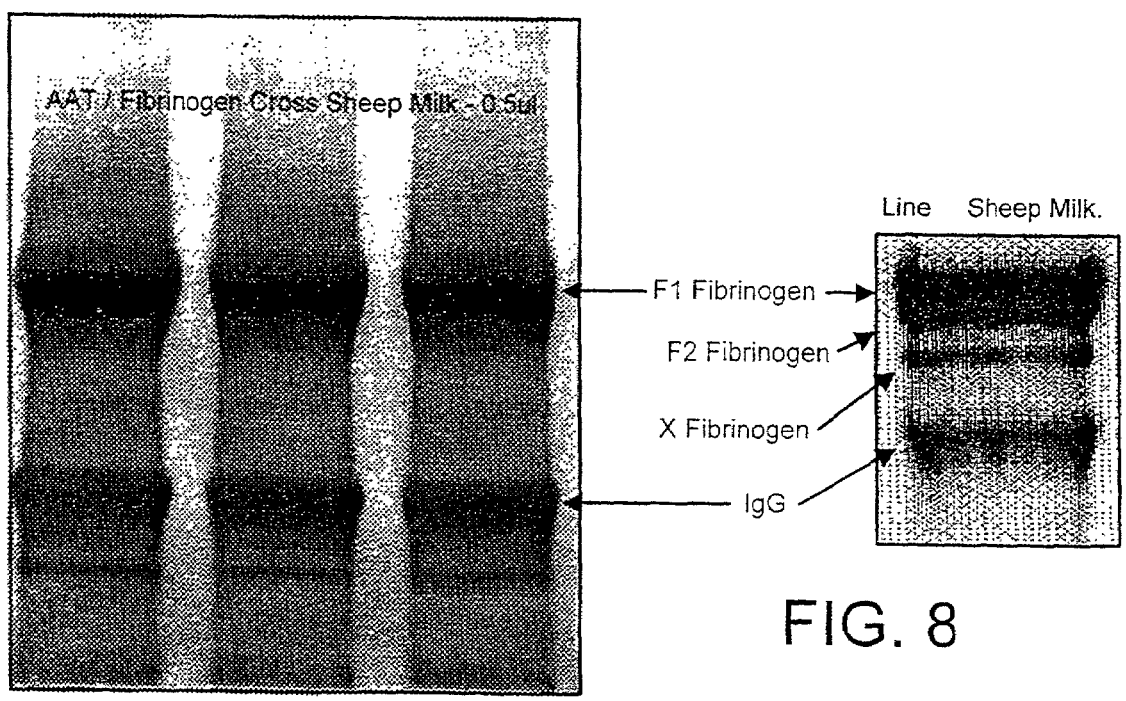

FIG. 8 shows an SDS-PAGE electrophoresis analysis under non-reducing conditions of the protein composition of the milk of sheep transgenic for both AAT and fibrinogen, and milk from sheep transgenic for fibrinogen only.

Figure 9:
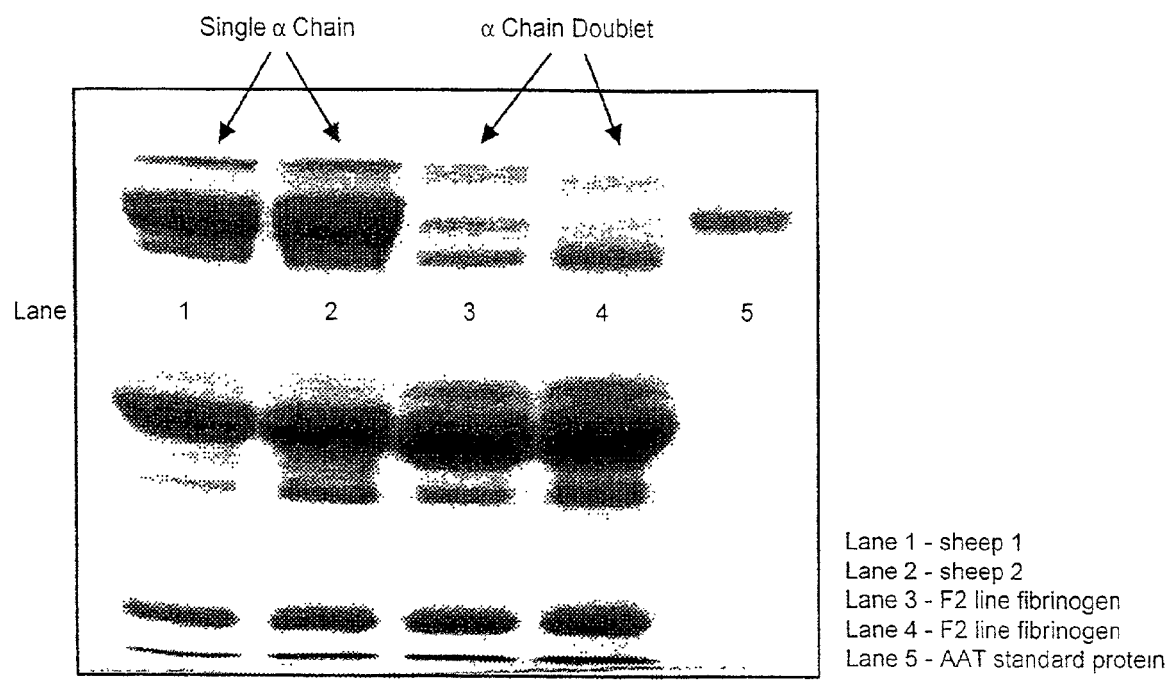

FIG. 9 shows an SDS-PAGE electrophoresis analysis under reducing conditions, showing milk from sheep transgenic for both AAT and fibrinogen and milk from sheep transgenic for fibrinogen only. Lane 1 is AAT-fibrinogen sheep 1; lane 2 is AAT-fibrinogen sheep 2; lanes 3 and 4 are F2 line fibrinogen sheep; lane 5 is AAT standard protein.

Figure 10:
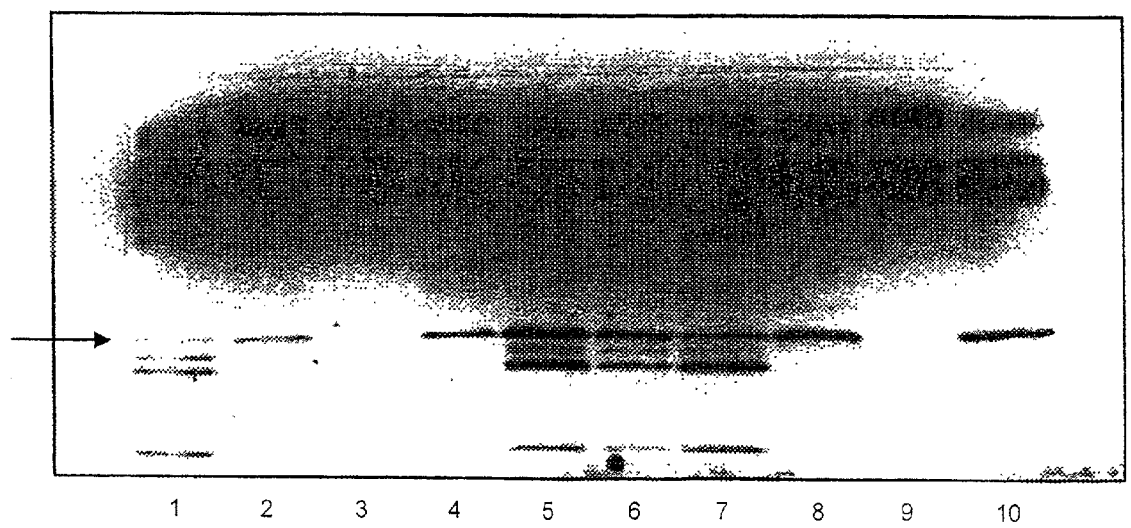

FIG. 10 shows a Western blot analysis of individual sheep milk from AAT-fibrinogen transgenic sheep and from fibrinogen-only transgenic sheep. Track 1 shows poor quality milk showing substantial degradation; tracks 2, 4 to 8 and 10 show single transgenic milk showing variable degradation; tracks 3 and 9 show milk from sheep transgenic for AAT and fibrinogen.

Figure 11:
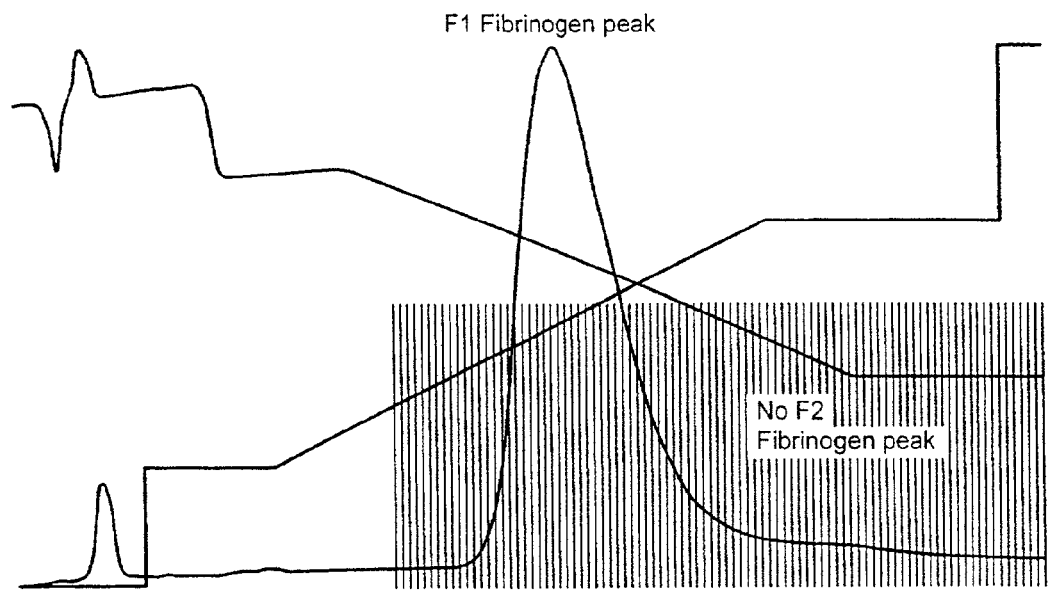

FIG. 11 shows an elution profile of milk from AAT-fibrinogen transgenic sheep, separated by HIC.

Figure 12:
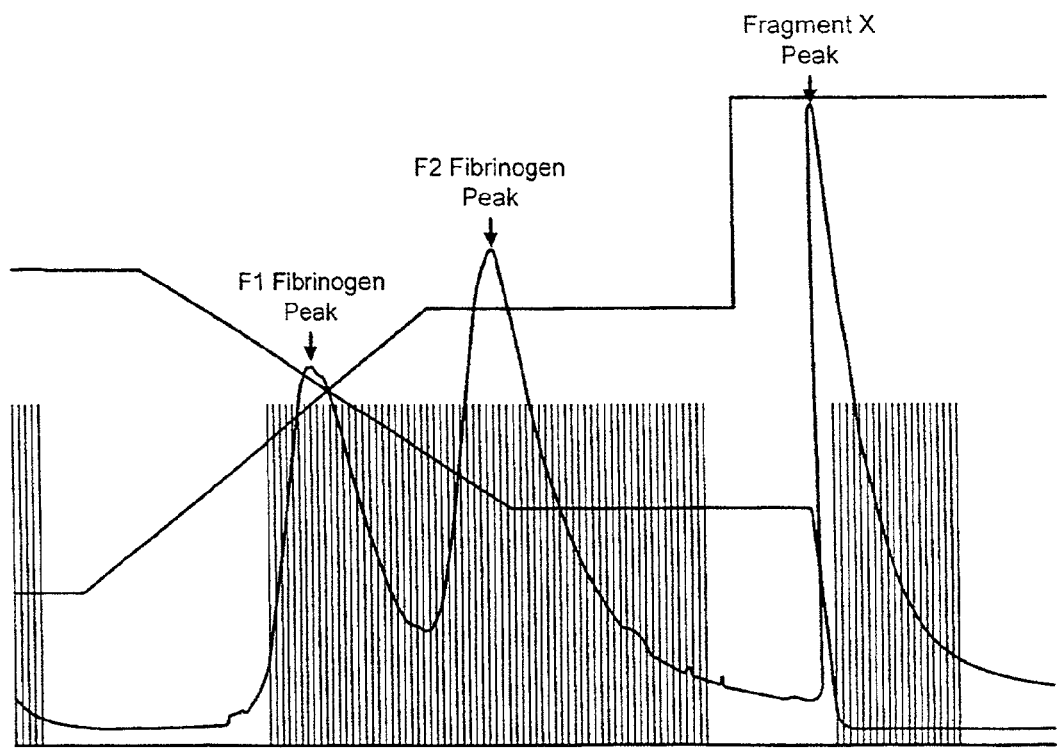

FIG. 12 shows an elution profile of milk from fibrinogen-only transgenic sheep, separated by HIC.

Figure 13A:
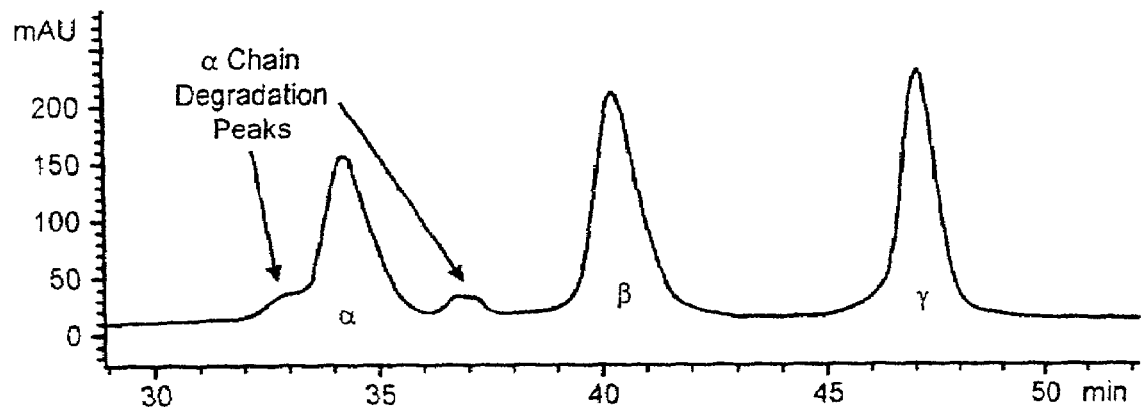
Figure 13B:
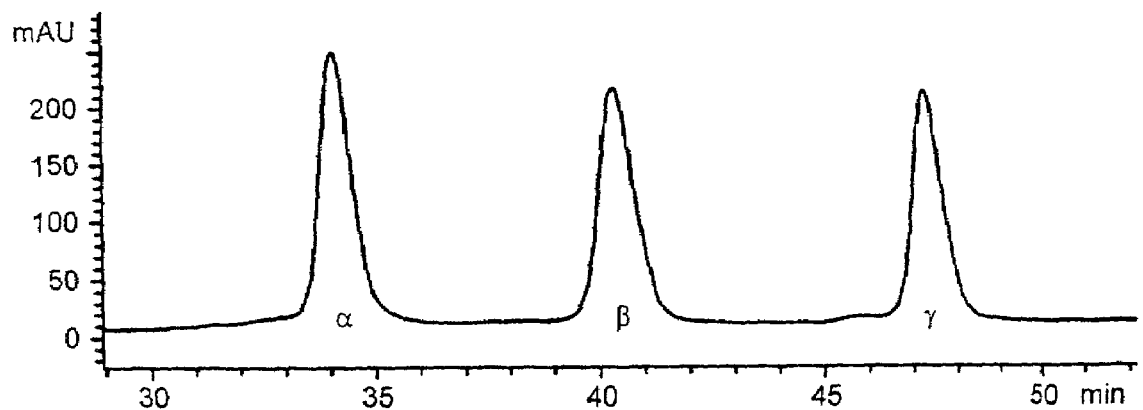

FIG. 13 shows elution profiles from reverse phase chromatography performed on milk from line F3 fibrinogen-only transgenic sheep (FIG. 13A) and from AAT-fibrinogen transgenic sheep (FIG. 13B). Individual fibrinogen chains are annotated. The wavelengths for both were 214 nm.

FIG. 14 shows the HIC elution profile of AAT-fibrinogen transgenic sheep.

FIG. 15 is an optical density curve showing the clotting of fibrinogen purified from fibrinogen-only transgenic sheep (line 1) and from AAT-fibrinogen transgenic sheep (line 2).

EXAMPLES

General

Where not specifically detailed, recombinant DNA and molecular biological procedures were after Maniatis et al ("Molecular Cloning" Cold Spring Harbor (1982)) "Recombinant DNA" *Methods in Enzymology* Volume 68, (edited by R. Wu), Academic Press (1979); "Recombinant DNA part B" *Methods in Enzymology* Volume 100, (Wu, Grossman and Moldgave, Eds), Academic Press (1983); "Recombinant DNA part C" *Methods in Enzymology* Volume 101, (Wu, Grossman and Moldgave, Eds), Academic Press (1983); and "Guide to Molecular Cloning Techniques", *Methods in Enzymology* Volume 152 (edited by S. L. Berger & A. R. Kimmel), Academic Press (1987). Unless specifically stated, all chemicals were purchased from BDH Chemicals Ltd, Poole, Dorset, England or the Sigma Chemical Company, Poole, Dorset, England. Unless specifically stated all DNA modifying enzymes and restriction endonucleases were purchased from BCL, Boehringer Mannheim House, Bell Lane, Lewes, East Sussex BN7 1LG, UK. [Abbreviations: bp=base pairs; kb=kilobase pairs, AAT=alpha1-antitrypsin; BLG=beta-lactoglobulin; FIX=factor IX; *E. coli=Escherichia coli;* dNTPs=deoxyribonucleotide triphosphates; restriction endonucleases are abbreviated thus e.g. BamHI; the addition of -O after a site for a restriction endonuclease e.g. PvuII-O indicates that the recognition site has been destroyed]

Construction of Transgenic Animals

Sheep

The generation of transgenic sheep is described in detail in International Patent Application No. WO-A-8800239 (Pharmaceutical Proteins Ltd) and by Simons, Wilmut, Clark, Archibald, Bishop & Lathe (1988) *Biotechnology* 6, 179–183.

The identification of transgenic sheep is described in detail in International Patent Application No. WO-A-8800239 (Pharmaceutical Proteins Ltd).

Example 1

Figure 1:
FIG. 1 is an SDS-PAGE which shows that AAT is hardly effective as an inhibitor against plasmin (in vitro). Lane 1 is fibrinogen (4 mg/ml) and AAT (1 mg/ml) with no plasmin; lane 2 is fibrinogen (4 mg/ml) and AAT (1 mg/ml) plus plasmin at 6 μg/ul; lane 3 is fibrinogen (4 mg/ml) and AAT (0.5 mg/ml) plus plasmin at 6 μg/ml.

An experiment was carried out to determine the effectiveness, in-vitro, of AAT at inhibiting plasmin. To a series of tubes containing fibrinogen at 4 mgml was added AAT at concentrations of 0.5 mg/ml and 1 mg/ml. To these tubes was then added plasmin (3 ug) giving an AAT: plasmin ratio of either 83:1 or 166:1 based on mass and 55:1 or 110:1 based on moles. The tubes were then incubated at 37° C. and results obtained from SDS-PAGE (see FIG. 1).

The results from this experiment show that even with the highest amount of AAT present, representing 110 molecules of AAT for every molecule of plasmin, there is significant degradation of fibrinogen after 4 h at 37° C.

Example 2

Increased Stability of AAT Milk Over Non-AAT Milk

Method

Aliquots (1 ml) of skimmed AAT milk (from a transgenic ewe which expresses the AAT at a level of approximately at 13 g/l) and skimmed non-AAT milk (from a ewe) were incubated at 37° C. for a period of 18 days to simulate accelerated aging. After this period visual inspection of the milks revealed that the non-AAT milk had separated into two phases while the AAT milk had the outward appearance of fresh milk. Both of the tubes were mixed and the contents added to 5 ml of 25 mM Tris-Acetate buffer at a pH of 4.6. This solution was mixed and then centrifuged at 2000 rpm for 10 min to promote precipitation of the casein fraction. The precipitated casein pellets were then washed with water before resuspending the casein in 2.5 ml of 8M urea in TBE buffer. To each tube was then added Dithioltheitol (DTT) to a final concentration of 2 mM.

Each of the samples was then diluted 1 in 5 with 6M urea in 20 mM Tris-Acetate buffer, pH 5.0 and 500 ul injected onto a 1 ml Resource S (Amersham Pharmacia Biotech) cation exchange column. Chromatography was carried out at 1 ml/min with bound protein being eluted utilising a gradient to 0.3M NaCl over 40 column volumes. Sample of fresh AAT milk and fresh non-AAT milk were treated exactly as above and were also run on the cation exchange column.

Results

Figure 2:
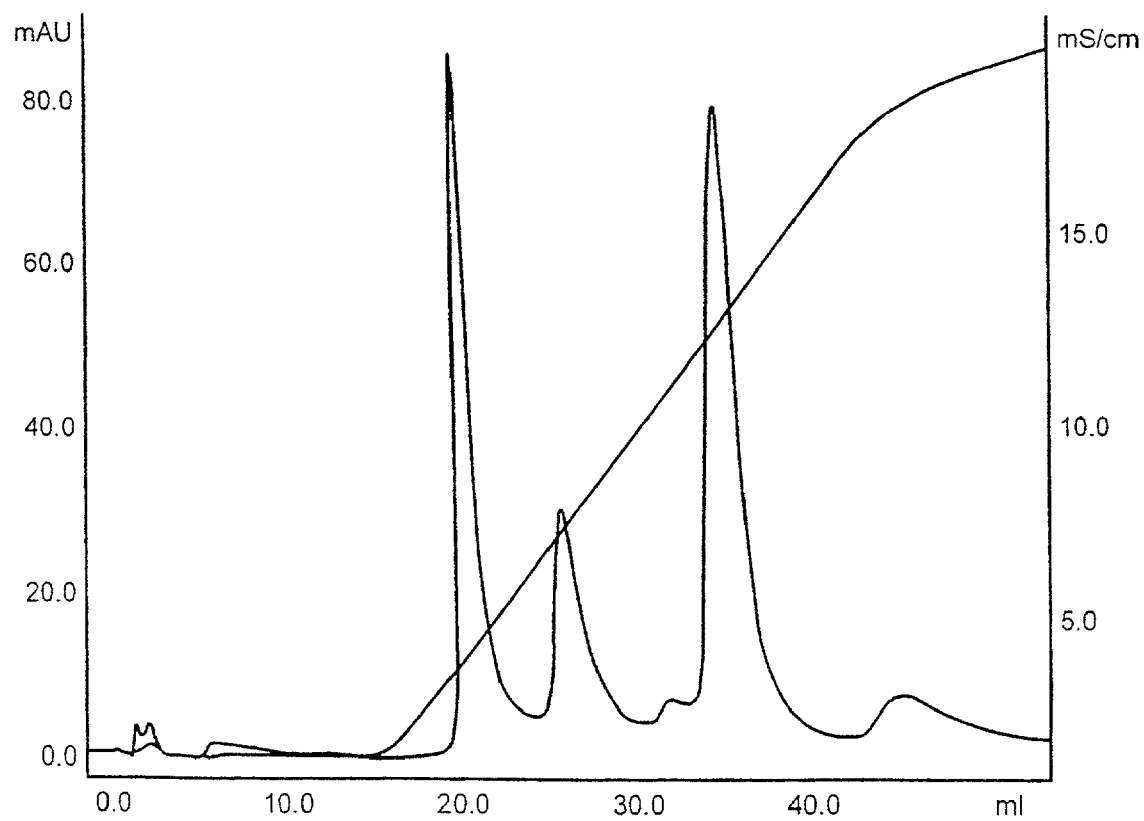
FIG. 2 is a chromatogram showing the resolution of casein proteins in milk after their precipitation from milk. The wavelength of the UV was 280 nm.
Figure 3:
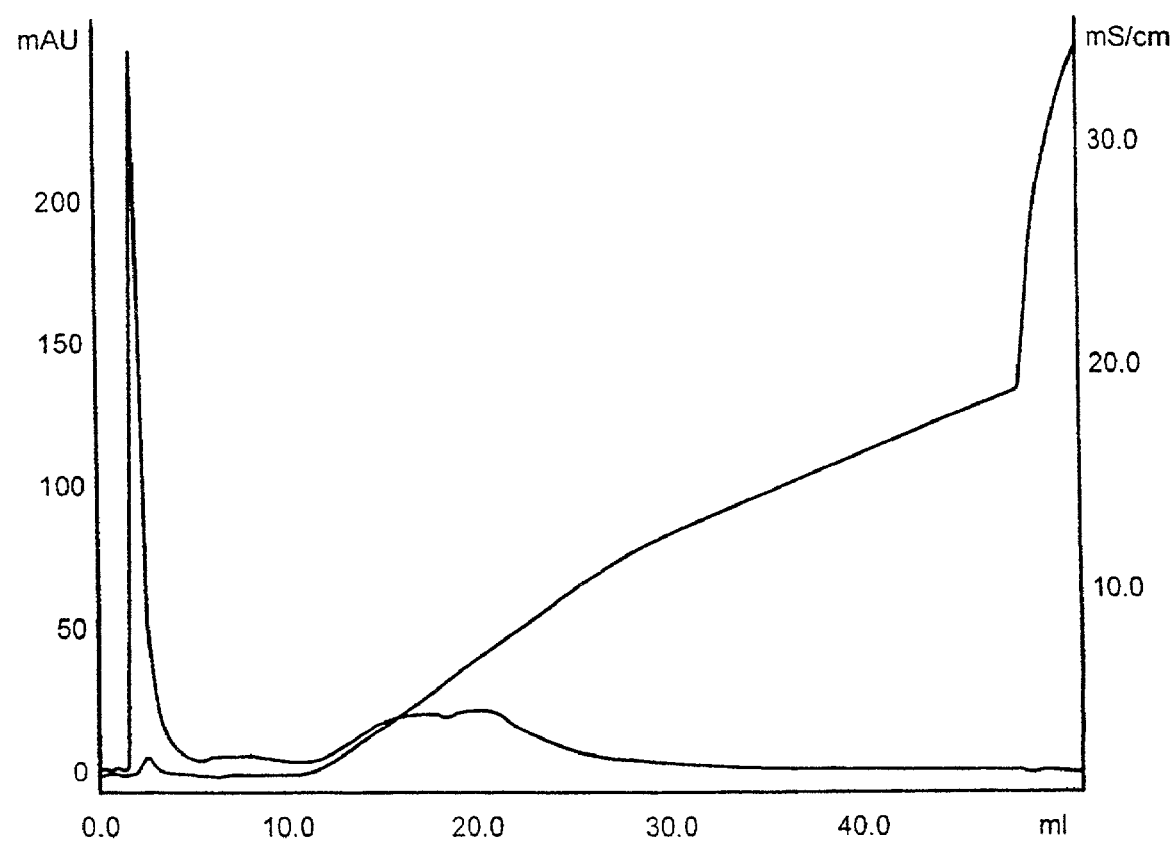
FIG. 3 is a chromatogram showing non-AAT milk after 18 days incubation at 37° C. The wavelength of the UV was 280 nm.
Figure 4:
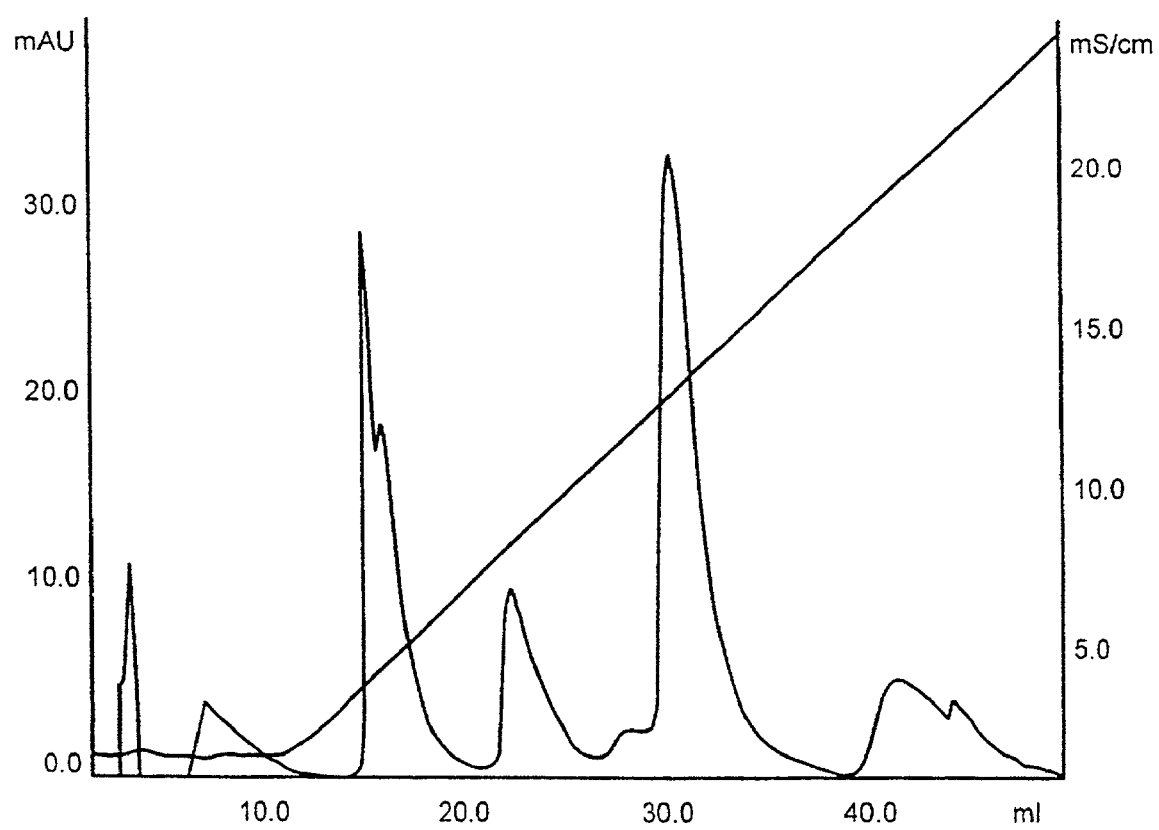
FIG. 4 is a chromatogram showing AAT milk before incubation. The wavelength of the UV was 280 nm.
Figure 5:
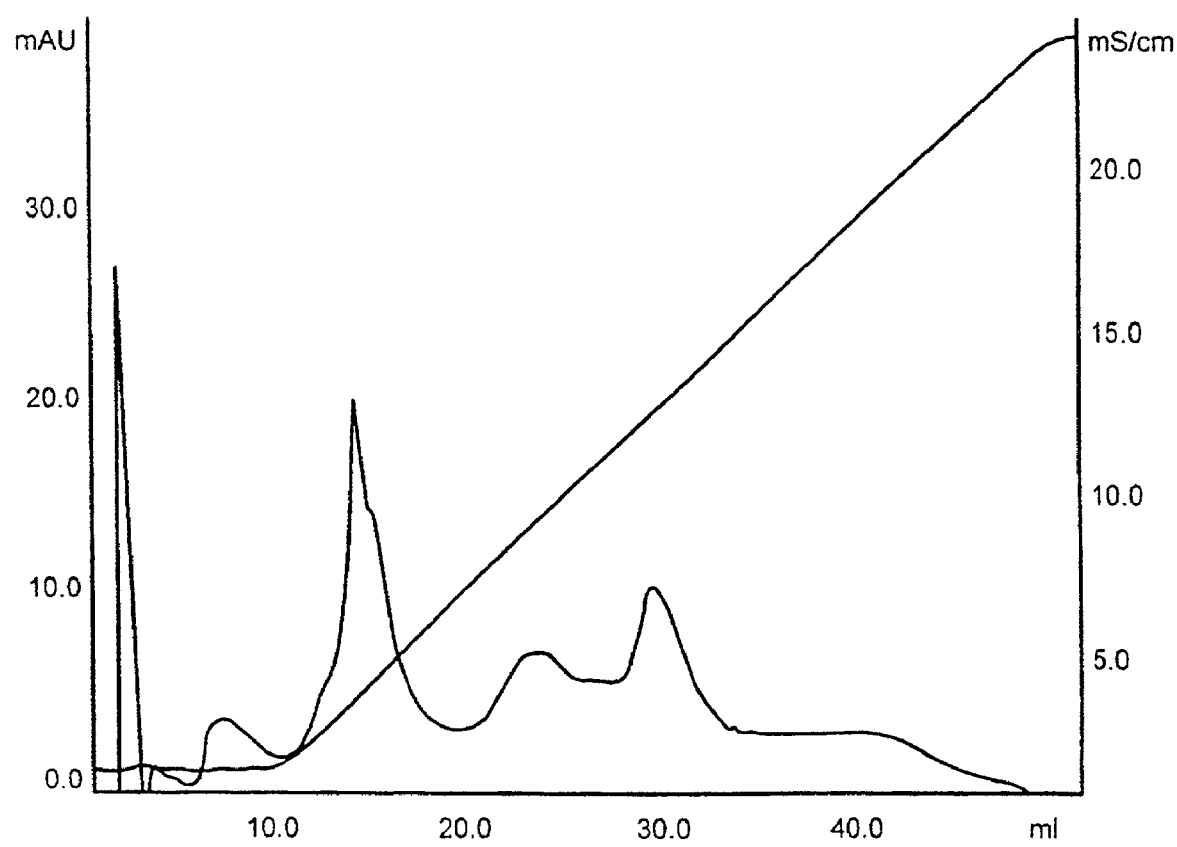
FIG. 5 is a chromatogram showing AAT milk before and after incubation at 37° C. for 18 days. The wavelength of the UV was 280 nm.

As shown in the chromatogram presented as FIG. 2, complete resolution of the casein proteins in milk is achievable after their precipitation from milk. The order of elution from the column is $\beta$ followed by $\kappa$ followed by $\alpha s_1$ followed by $\alpha_2$. When comparing this chromatogram with the chromatogram presented in FIG. 3, which represents non-AAT milk after 18 days incubation at 37° C., it is very easy to see that there is no resolution obtained on the chromatographic separation demonstrating that extensive structural damage has occurred to the caseins presumably as a result of extensive proteolysis. In comparison, when examining the chromatograms presented in FIG. 4 & FIG. 5 representing AAT milk before and after incubation at 37° C. respectively it can be seen that before incubation, the chromatogram is very similar to that obtained with non-heated non-AAT milk. After incubation at 37° C. for 18 days, the chromatogram retains its overall pattern demonstrating that the structure of the caseins remains relatively intact. It is interesting to note that the $\alpha s_1$ casein is probably most damaged as shown be a decrease in its peak height and area. This complies with reports in the literature suggesting that the $\alpha s_1$ casein is most prone to proteolytic degradation.

Conclusions

The conclusions of this experiment are as follows
1) Visual examination of accelerated aging samples of AAT and non-AAT milk reveals that non-AAT milk is significantly less stable that AAT milk
2) Cation exchange chromatography of casein confirms that in aged samples of non-AAT milk, significant structural changes occur in the casein fraction resulting in an absence of resolution on the chromatographic step. These structural changes are presumably due to proteolysis.
3) Cation exchange chromatography of casein in aged AAT milk reveals that although a degree of casein degradation has taken place, the overall resolution obtained on the column is similar to that obtained with non-aged AAT milk.
4) Degradation of $\alpha s_1$ and $\alpha s_2$ casein appears to occur before $\beta$ casein as would be expected from the literature.

Example 3

Generation and Screening of AAT and Fibrinogen Transgenic Sheep

The sheep (a and b) were screened in two ways in order to confirm that they were transgenic for both AAT and the fibrinogen constructs.

Fibrinogen Screening

The Sheep DNA was digested with the restriction enzyme AvrII. This enzyme produces fragments from the three fibrinogen chains of a specific molecular weight. These fragments are separated on the basis of size using a gel. The DNA on the gel is transferred to a DNA binding membrane (termed a blot). The blot is then probed with radioactive DNA made from the BLG (Beta-Lactoglobulin) gene control region common to all three chains. The control region binds to DNA of the same sequence, making any regions of similar sequence radioactive. The radioactivity can be detected by placing a photographic film against the region. The bands of radioactivity from the sheep can be compared with the known controls, 1 and 10 copy in FIG. 6. Lane A is a negative control; lane B is a 1 copy control; lane C is a 10 copy control; lane D is sheep a and lane E is sheep b.

The bands are of the correct size and confirm that this sheep is transgenic for all three of the fibrinogen genes. The probe also detects the sheep's own BLG and the AAT in the sheep, however these are not resolved in the gel.

AAT Screening

The process of AAT screening is the same as the fibrinogen screening, except that the restriction enzyme BamHI is used. This cuts the DNA into different size bands, so different bands are produced. See FIG. 7. Lane A is sheep 1; lane B is sheep b; lane C is a negative control; lane D is a 10 copy control; lane E is a 20 copy control. The bands seen are the BLG control region of the AAT transgene, the sheep's own BLG and the BLG control region of the fibrinogen transgenes. The enzyme does not resolve the fibrinogen chains separately. Knowledge of the predicted restriction pattern with BamHI confirms that a fragment consistent with the AAT transgene is present.

Example 4

Analysis of Milk from Transgenic Sheep

DNA from two sheep, cross bred from individual AAT and fibrinogen lines identified as sheep 1 and 2 were analysed by the process of Southern blotting and found to be positive for both the human proteins α1-antitrypsin (AAT) and fibrinogen. Both sheep were induced to lactate by hormonal treatment with milkings undertaken twice daily. The average daily milk yield was measured at lactation continued for about six weeks.

a) RID Analysis of Sheep Milk

To quantitate the concentration of each of the human proteins expressed in the milk of the sheep the method of Radial Immunodiffusion (RID) was used. Commercial RID kits produced by The Binding Site company were employed. By comparing the diameter of the rings produced by the milk samples from the sheep to both human AAT and Fibrinogen standards supplied in the RID kits accurate concentrations were attained. The results are detailed below.

| AAT RID Results | |
|---|---|
| | Ring Diameter |
| Human AAT Standard | |
| 0.28 mg/ml | 4.1 mm |
| 0.84 mg/ml | 4.9 mm |
| 1.40 mg/ml | 7.1 mm |
| 1.68 mg/ml | 7.6 mm |
| 2.80 mg/ml | 9.1 mm |
| Sheep Milk in 1 in 10 Dilution | |
| Sheep 980082 | 6.0 mm |
| Sheep 980417 | 5.8 mm |

This data equates to a neat AAT concentration of 10.5 mg/ml for sheep 1 and 9.6 mg/ml for sheep 2 in the sheep milk.

| Fibrinogen RID Results | |
|---|---|
| | Ring Diameter |
| Human Fibrinogen Standard | |
| 0.45 mg/ml | 4.1 mm |
| 1.35 mg/ml | 5.1 mm |
| 2.25 mg/ml | 5.9 mm |
| 2.70 mg/ml | 6.4 mm |
| 4.50 mg/ml | 7.9 mm |
| Sheep Milk in 1 in 5 Dilution | |
| 980082 | 5.0 mm |
| 980417 | 5.4 mm |

This equates to a neat fibrinogen concentration in the sheep milk of 6.3 mg/ml for sheep 1 and 8.1 mg/ml for sheep 2.

b) SDS-Page Analysis of Sheep Milk

By SDS-PAGE electrophoresis analysis under non-reducing conditions, the protein composition of the sheep milk could be analysed. More precisely the identification of any fibrinogen degradation products such as fragments X and Y was possible A gel comparing the milk from the double transgenic sheep to previously milked sheep from line F which expressed only fibrinogen, i.e. no AAT, is shown in FIG. 8.

The fibrinogen produced by the double transgenic animals comprises the protein only in the F1 form. The milk contains none of the products associated with degradation such as F2 fibrinogen and fragments X and Y. The milk obtained from an animal solely transgenic for fibrinogen clearly displays the degradation product fragment X as well as F2 fibrinogen.

SDS-PAGE electrophoretic analysis undertaken under reducing conditions provides data regarding the individual chain subunits of the fibrinogen protein. Again by comparing milk from sheep transgenic for both AAT and fibrinogen to sheep expressing only fibrinogen, sheep from line F2 differences are clearly observable. FIG. 9 shows the two forms of fibrinogen.

The fibrinogen expressed by the two forms of sheep construct clearly contains the α, β, and γ chains characteristic of the fibrinogen protein. However, interesting differences arise when comparing the α chain subunits. In the single transgenic fibrinogen milk two α chain subunits are observed, indicated by a broad band on the scanned gel image. This is in direct contrast to the fibrinogen expressed by the AAT/Fibrinogen dual construct animals, which clearly displays only a single α chain. This again is evidence that practically no degradation of the fibrinogen occurs in sheep milk from animals positive for both AAT and fibrinogen.

c) Analysis of Sheep Milk by Western Blot

Further evidence of the low incidence of proteolytic damage to fibrinogen produced in the milk of AAT and fibrinogen doubly transgenic sheep is provided by Western Blot analysis. Milk from single and double transgenic lines is first resolved on the basis of molecular mass into protein components by gel analysis. A stable 'print' of the gel is then made by electrophoretic transfer to a plastic membrane. This membrane is then exposed to a polyclonal antibody to fibrinogen and washed extensively to remove unbound antibody. Bound antibody is detected by a second antibody bound to a reporter enzyme, horse radish peroxidase. Subsequently, after extensive washing to remove the unbound second antibody, all fibrinogen subunits and their proteolytic fragments are visualised using a light-emitting peroxidase substrate and a permanent record taken on photographic film.

Fibrinogen expressed in the absence of AAT is subject to a varying degree of proteolysis depending on the individual sheep and the stage of lactation—with more proteolysis later on. Although much of the degraded material is removed on purification there is still a proportion of proteolytically clipped alpha chain and the product contains both F1 and F2 species—as seen with plasma-derived fibrinogen. However, the range of processing enzymes in milk is more limited than in plasma and F2 in milk is due mostly to a cleavage event around amino acid 220. This produces a well-defined truncated alpha chain species seen both on SDS Page analysis of purified product and, in the case being discussed, on a western blot of milk (FIG. 10) Truncated chain indicated by the arrow in the left.

FIG. 10 clearly shows that there is an undetectable level of truncated alpha chain in both of the AAT and fibrinogen double transgenic milks analysed (Tracks 3 and 8). This contrasts with the varying and sometimes substantial degree of degradation seen in the singly transgenic milks (all other tracks).

d) Hydrophobic Interaction Chromatography (HIC) Analysis

The process of HIC is utilised to separate the F1, F2 and X forms of fibrinogen. The fibrinogen is purified from the milk by three rounds of precipitation. The preparation is then loaded on to a butyl sepharose column. Contaminants are removed by prewashing the column and then F1, F2 and fragment X are eluted in order by a decreasing gradient of ammonium sulphate.

The elution profile in FIG. 11 produced by analysis of purified fibrinogen from AAT/Fibrinogen the double transgenic sheep shows that only F1 fibrinogen is present, no F2 or X is detectable. However, in singly transgenic sheep purified fibrinogen, result shown in FIG. 12, both F1, F2 and X forms of the protein are present with the F1 from being the minor species. This is further evidence that the co-expression of AAT and fibrinogen prevents fibrinogen degradation and without the presence of AAT, degradation of the fibrinogen protein occurs.

e) Reverse Phase Chromatography (RPC) of Fibrinogen

The process of RPC was utilised to analyse precisely the chain stoicheiometry makeup of the fibrinogen produced by the transgenic sheep. Samples of fibrinogen post HIC purification were reduced in the presence of 10 mM Dithiothreitol and 6M Guanidine, a process which releases the three different chains of fibrinogen from the intact protein. Samples were analysed using a Vydac 4.6×150 mm C4 column with 0.1% TFA and $CH_3CN$ buffers. The elution profiles in FIG. 13 show that fibrinogen from the singly transgenic fibrinogen sheep displays signs of α chain degradation, which is typical of the presence of F2 and X fibrinogen. As a consequence the α chain is not the dominant species of the protein. This result is in direct contrast to that produced by fibrinogen from the AAT/Fibrinogen double transgenic sheep which exhibits no sign of α chain degradation. Therefore the α chain is the dominant species and it is apparent that no F2 or X forms of fibrinogen are present.

f) Stability Analysis of the Fibrinogen

Milk from the AAT/fibrinogen dual transgenics was incubated at 30° C. for 18 hours. Following this time the milk whey was partially purified three rounds of precipitation prior to being subjected to HIC analysis using the butyl sepharose column. This would detect the degradation of any F1 fibrinogen to F2 and fragment X due to instability of the protein in milk.

The HIC elution profile, shown in FIG. 14, of the fibrinogen from AAT/Fibrinogen cross sheep displays only the F1 form of the fibrinogen protein. Thus no degradation due to instability has occurred.

g) Fibrinogen Co-Expressed with AAT is Functionally Equivalent to Fibrinogen Expressed Alone Purified fibrinogen from double transgenic milk was shown to be functionally equivalent to material made from singly transgenic milk. This in turn has been shown to be functionally equivalent to plasma-derived fibrinogen. In the present example the formation of clots at low thrombin and fibrinogen concentrations is followed by the change in optical density.

Optical density (OD) measurements are used to quantify the time-dependent change in opacity of the fibrinogen in gels. This opacity is measured as the increase in the OD over time. This change in OD is due to the light scattering from the fibrin fibres rather that to the increased absorbance. The coarser the gel structure, the thicker the fibrin fibres and the higher the OD. The finer the gel structure, the thinner the fibrin fibres, and the lower the OD. The interesting parameters in this assay are the rate of the initial increase in OD, a measure of the rate of gelation, and the final OD, a measure of the coarseness of fibres (coarse fibres scatter more light).

500 µl of either singly transgenic fibrinogen or doubly transgenic fibrinogen at 0.15 mg/ml in tris buffered saline plus 5 mM $CaCl_2$ was added to plastic micro cuvettes. 50 µl of purified plasma-derived thrombin (Enzyme Research Laboratories) at 0.6 units/ml was added to each cuvette followed by quick mixing. The absorbance at 350 nm was recorded for 20 minutes. The results are shown in FIG. 15.

A comparison of the OD profiles for fibrinogen expressed alone or in the presence of AAT shows that both the rates of clotting and the coarseness of the final fibres are highly similar (FIG. 15) and therefore, the two materials are functionally equivalent. Although the single transgenic material appears to produce coarser fibres it is not possible to attach significance to this from a single assay and the results should be regarded as indistinguishable.

The invention claimed is:

1. A method for stabilizing heterologous fibrinogen expressed in the milk of a transgenic non-human mammal comprising co-expressing, with said heterologous fibrinogen in the milk of said mammal, alpha-1-antitrypsin operably linked to a milk-protein specific promoter.

2. The method, as claimed in claim 1, wherein the mammal is a sheep, cow, goat, rabbit, mouse, camel, water-buffalo, pig or horse.

* * * * *